United States Patent [19]
Sanberg et al.

[11] Patent Number: 6,034,079
[45] Date of Patent: Mar. 7, 2000

[54] NICOTINE ANTAGONISTS FOR NICOTINE-RESPONSIVE NEUROPSYCHIATRIC DISORDERS

[75] Inventors: Paul R. Sanberg, Spring Hill; Roland D. Shytle, Lutz; Archie A. Silver, Tampa, all of Fla.

[73] Assignee: University of South Florida, Tampa, Fla.

[21] Appl. No.: 09/198,882

[22] Filed: Nov. 23, 1998

Related U.S. Application Data

[63] Continuation-in-part of application No. PCT/US98/16634, Aug. 11, 1998, which is a continuation-in-part of application No. PCT/US97/20689, Nov. 7, 1997, which is a continuation-in-part of application No. 08/935,364, Sep. 22, 1997, abandoned
[60] Provisional application No. 60/055,234, Aug. 11, 1997.
[51] Int. Cl.[7] .................... A61K 31/54; A61K 31/505; A61K 31/445; A61K 31/13
[52] U.S. Cl. .................... 514/225.8; 514/258; 514/322; 514/327; 514/661
[58] Field of Search .................... 514/225.8, 258, 514/322, 327, 661

[56] References Cited

U.S. PATENT DOCUMENTS

| | | | |
|---|---|---|---|
| 2,831,027 | 4/1958 | Pfister, III et al. | 260/563 |
| 2,894,987 | 7/1959 | Gustav et al. | 260/563 |
| 3,148,118 | 9/1964 | Thesing et al. | 167/65 |
| 3,164,601 | 1/1965 | Thesing et al. | 260/294.7 |
| 4,837,218 | 6/1989 | Olney | 514/646 |
| 4,891,380 | 1/1990 | Wiiliams et al. | 514/353 |
| 5,554,610 | 9/1996 | Williams et al. | 514/223.2 |
| 5,574,052 | 11/1996 | Rose et al. | 514/343 |
| 5,583,140 | 12/1996 | Bencherif et al. | 514/299 |
| 5,691,365 | 11/1997 | Crooks et al. | 514/343 |
| 5,859,004 | 1/1999 | Olesen | 514/214 |

OTHER PUBLICATIONS

Shieh, et al. (1996) Biology of Reproduction, vol. 54, May, pp. 987–992 Sexual Differences in the Diurnal Changes . . . of Neuron Activity in Rat: Role of Cholinergic Control.
Sano Coporation website (1997).
Shytle, et al. (1996) Drug Development Research, vol. 38, pp. 290–298 "Transdermal Nicotine for Tourett's Syndrome".
(1989) The Merk Index, p. 905 "5654. Mecamylamine".
Stone, et al. (1962) Journal of Medicine & Pharm. Chemistry, vol. 5(4), pp. 665–690 "Chemistry and Structure–Activity Relationship of Mecamylamine and Derivatives".
Seumaru, et al.; Naonyn–Schmledeberg's Arch pharmacol (1994) 350:153–157 "Characteristics of tail–tremor induced by nicotine in rats".
Psychopharmacologia (Berl.) 46, 119–121 (1976) "Nicotine–Like . . . after . . . Mecamylamine in . . . rats".
Pharmacol Ther, vol. 74, No. 1, pp. 21–25, 1997 "Nicotine for the Treatment of Tourette's Syndrome".

Shytle, et al; Int'l Weekly Journal of Science, vol. 384, pp. 18–19 "Nicotine, tabacco and Addiction" (1997).
Sanberg, et al.; pp. 35–41 (1997) "Nicotine as a Therapeutic Adjunct for Tourett's Syndrome".
The Lancet, Mar. 12, 1988, p. 592 "Nicotine Gum & Haloperidol in Tourette's Syndrome".
The Lancet, vol.. 342, Jul. 17, 1993, p. 182 "Transdermal nicotine patch . . . in Tourette's Syndrome".
Sanberg, et al.; Biomed & Pharmacother., 43 (1989) 19–23 "Nicotine . . . with Tourette's Syndrome".
McConville et al.; Amer. J. Psychiatry 148:6, Jun. 1991, p. 793 "Nicotine . . . in Tourette's Syndrome".
Emerivch et al.; Pharm. Biochem. & Bevhav. vol. 38 (1991), pp. 875–880 "Nicotine . . . Locomotor Hypoactivity".
Emerich, et al.; Psychopharm. Bulletin. vol. 27:3 (1991), pp. 385–390 "Nicotine . . . of Haloperidol".
McConville, et al.; Biol. Psychiatry vol. 31 (1992) pp. 832–840 The Effects . . . in Tourette's Disorder.
Sanberg, et al.; Pharmacol. Biochem & Behavior vol. 46 (1993) pp. 303–307 Nicotine . . . Striatal Mechanisms.
Silver, et al.; J. Amer. Child & Adolesc. Psych. vol. 35 (12) (1996) pp. 1631–1636 "Case Study . . . In Tourette's Syndrome".
Shytle, et al.; Tourette Syn. Assoc. Summer 1997, 25(1): 1,3,7 Researchers Exploring . . . TS Treatment.
Schonenberger, et al.; Helvetica Chimica Acta, vol. 69 (1986) pp. 283–287 "Preparation of Optically Active . . .".
Hsu, Walter; HAVMA, vol. 176, No. 10 (May 1980), pp. 1166–69 "Toxicity and Drug Interactions of Levamisole".
Ballivet, et al.; JMB, 2296, Academic Press Limited, pp. 261–269 "Nicotine Acetylcholine . . . elegans" (1996).
Banerjee, et al.; Biochemical Pharmacology vol. 40, No. 9, pp. 2105–2110, 1990 "[3H] Mecamylamine Binding to Rat Brain Membranes".
Bianchi & Tomasi; Pharmacology 10:226–237, 1973 "Central Nervous System . . . Standard Anti–Parkinson Drugs".
Rupniak et al.; Brit. J. Pharmacol. 1994, 113(4): 1487–1493 "Antinociceptive and Toxic Effects . . . Attributable to Nicotinic Agonist Activity".

*Primary Examiner*—Kimberly Jordan
*Attorney, Agent, or Firm*—Barbara J. Luther

[57] ABSTRACT

Nicotine-responsive neuropsychiatric disorders can be treated by administering a nicotine antagonist, particularly mecamylamine. Combination therapy of mecamylamine with a neuroleptic drug also is disclosed. The neuropsychiatric disorders include Tourette's syndrome, schizophrenia, depression, bipolar disorder, tremors, attention deficit hyperactivity disorder, obsessive-compulsive disorder, hemidystonia, rage outbursts and tardive dyskinesia.

11 Claims, 1 Drawing Sheet

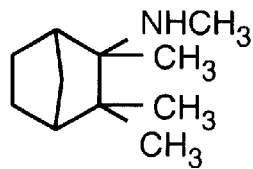
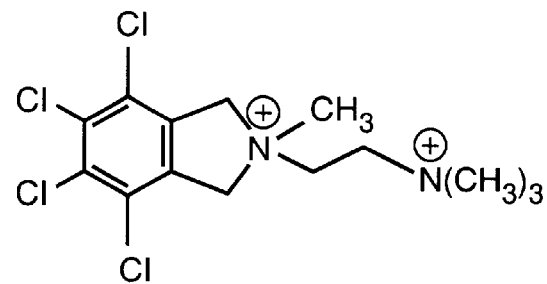
MECAMYLAMINE        CHLORISONDAMINE
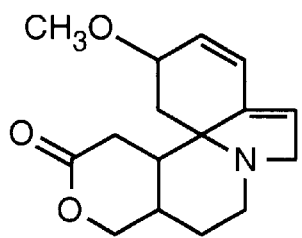
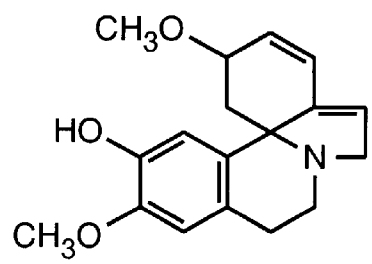
β-DIHYDROERYTHROIDINE        ERYSODINE
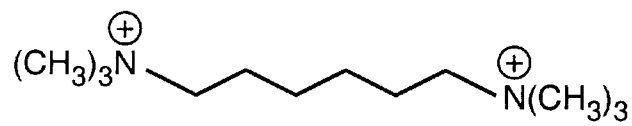
HEXAMETHONIUM
FIG._1

NICOTINE ANTAGONISTS FOR NICOTINE-RESPONSIVE NEUROPSYCHIATRIC DISORDERS

This application is a continuation-in-part of Application No. PCT/US98/16634, filed on Aug. 11, 1998, now pending, which is a continuation-in-part of Application No. PCT/US97/20689, filed on Nov. 7, 1997, now pending, which is a continuation-in-part of U.S. Non-Provisional Application No. 08/935,364, filed on Sep. 22, 1997, now abandoned, which is a continuation-in-part of U.S. Provisional Application No. 60/055,234, filed Aug. 11, 1997, now abandoned.

BACKGROUND

1. Field of the Invention

The present invention is in the field of pharmacotherapy of nicotine-responsive neuropsychiatric disorders by administering a nicotine antagonist alone, particularly mecamylamine, or in combination with a neuroleptic agent. Examples of such disorders are schizophrenia, bipolar disorder, obsessive compulsive disorder, attention deficit hyperactivity disorder, Tourette's syndrome, and other movement disorders.

2. Background Information

Tourette's syndrome (TS) is an autosomal dominant neuropsychiatric disorder characterized by a range of symptoms, including multiple motor and phonic tics. It is a hyperkinetic movement disorder expressed largely by sudden, rapid, brief, recurrent, nonrhythmic, stereotyped motor movements (motor tics) or sounds (phonic tics), experienced as irresistible impulses but which can be suppressed for varying lengths of time (Tourette Syndrome Classification Study Group, Arch Neurol 50: 1013–16). Motor tics generally include eye blinking, head jerking, shoulder shrugging and facial grimacing, while phonic or vocal tics include throat clearing, sniffling, yelping, tongue clicking and coprolalia. The symptoms typically begin in childhood and range from relatively mild to very severe over the course of a patient's lifetime (Robertson M M, Br J Psychiatry, 154:147–169, 1989). Many TS patients also exhibit other neuropsychiatric abnormalities including obsessive compulsive symptoms (Pauls D L et al. Psychopharm Bull, 22:730–733, 1986), hyperactivity and attention deficits (Comings D E, Himes J A, Comings B G, J Clin Psychiatry, 51:463–469, 1990). Problems with extreme temper or aggressive behavior also are frequent (Riddle M A et al. Wiley Series in Child and Adolescent Mental Health, Eds. Cohen D J, Bruun, R D, Leckman J F, New York City, John Wiley and Sons, pp. 151–162, 1988; Stelf M E, Bornstein R A, Hammond L, A survey of Tourette syndrome patients and their families: the 1987 Ohio Tourette Survey, Cincinnati, Ohio Tourette Syndrome Association, 1988), as are school refusal and learning disabilities (Harris D, Silver A A, Learning Disabilities, 6(1):1–7, 1995; Silver A A, Hagin R A, Disorders of Learning Childhood, Noshpitz J D, ed. New York City: Wiley, pp. 469–508, 1990).

While the pathogenesis of TS is still unknown, excessive striatal dopamine and/or dopamine receptor hypersensitivity has been proposed (Singer H S et al. Ann Neurol, 12:361–366, 1982), based largely on the therapeutic effectiveness of dopamine receptor antagonists. T S is frequently treated with the dopamine antagonist haloperidol (Haldol®, McNeil Pharmaceutical, Raritan, N.J.), which is effective in about 70% of cases (Erenberg G, Cruse R P, Rothner, A D, Ann Neurol, 22:383–385, 1987; Shapiro A K, Shapiro E, Wiley series in child and adolescent mental health. Eds. Cohen D J, Bruun R D, Leckman J F, New York City, John Wiley and Sons, pp. 267–280, 1988). Other neuroleptics include pimozide (Shapiro E S et al. Arch Gen Psychiatry, 46:722–730, 1989), fluphenazine (Singer H S, Gammon K, Quaskey S. Pediat Neuroscience, 12:71–74, 1985–1986), and risperidone (Stamenkovic et al., Lancet 344:1577–78, 1994). An alternative medication frequently employed is the α-adrenergic agonist clonidine, which also is effective for associated attention deficit hyperactivity disorder (ADHD) but has only a 40% success rate for motor and vocal tics (Bruun R D, J Am Acad Child Psychiatry, 23: 126–133, 1984; Cohen D J et al. Arch Gen Psychiatry 37: 1350–1357, 1980). Other medications that have been used with varying degrees of effectiveness include clonazepam (Gonce M, Barbeau A. Can J Neurol Sci 4:279–283, 1977), naloxone (Davidson P W et al. Appl Res Ment Retardation 4: 1–4, 1983) and fluoxetine (Riddle M A et al. J Am Acad Child Adol Psychiatry 29: 45–48, 1990). One of the most commonly used medications is haloperidol (Erenberg G, Cruse R P, Rothner A D, Ann Neurol, 22:383–385, 1987). However, therapeutic doses of haloperidol have frequent side effects that affect compliance, including difficulty in concentration, drowsiness, depression, weight gain, parkinsonian-like symptoms—and with long-term use—tardive dyskinesia (Shapiro A K, Shapiro E, Tourette's syndrome and Tic Disorders: Clinical Understanding and Treatment. Wiley series in child and adolescent mental health. Eds. Cohen, D J, Bruun, R D, Leckman J F, New York City, John Wiley and Sons, pp. 267–298, 1988). The side effect of tardive dyskinesia is particularly bothersome because it may add additional abnormal, involuntary movements of the tongue, jaw, trunk and/or extremities.

Erenberg et al. (Erenberg G, Cruse R P, Rothner A D, Ann Neurol 22:383–385, 1987) found that most patients with TS stop using their haloperidol or other neuroleptic medications by age 16, often because of these side effects. After TS patients quit medication because of the side effects, they have less control over speech and movement, which disqualify many for full-time, responsible jobs. The public, including law enforcement officers, often identify the symptoms as intoxication. The unexpected movements and coprolalia cause great social difficulties.

Systemic or intracaudate injections of nicotine have been found to profoundly potentiate reserpine-induced catalepsy in rats (Montgomery S P, Moss D E, Manderscheid P Z, Marijuana 84. Eds. Harvey D J, Paton W D M, Oxford, England, IRL Press, pp. 295–302, 1985; Moss D E et al, Life Sci 44: 1421–1525, 1989). Follow-up studies demonstrated that low doses of nicotine could also potentiate haloperidol-induced catalepsy in rats (Sanberg P R et al, Biomedicine and Pharmacotherapy 43: 19–23, 1989; Emerich D F, Norman A B, Sanberg P R, Psychopharmacol Bull 27(3): 385–390, 1991; Emerich D F et al, Pharmacol Biochem Behav 38: 875–880, 1991). These preclinical findings suggested that nicotine might also potentiate the therapeutic properties of neuroleptics in treating hyperkinetic movement disorders such as TS.

In a preliminary clinical trial, ten TS patients continued to receive haloperidol and added chewing Nicorette® nicotine (2 mg) gum. The patients had rapid, striking and marked relief from tics and other TS symptoms which were not optimally controlled by haloperidol alone (Sanberg P R et al, Biomedicine and Pharmacotherapy 43:19–23, 1989). In two subsequent studies, nicotine gum reduced tics in patients already receiving haloperidol, while placebo gum had no effect (McConville B J et al, Am J Psychiatry 148:793–794, 1991; McConville B J et al, Biological Psychiatry, 31:832–840, 1992). However, the benefits of the gum were short lived (1–4 hours), and the bitter taste and gastrointestinal side effects limited compliance (McConville B J et al, Biological Psychiatry 31:832–840, 1992).

The 7 mg, 24-hour transdermal nicotine patch (Nicoderm® TNP) was tested in 11 TS patients who were not responding optimally to current neuroleptic treatment (Silver A A et al. The Effects of Nicotine on Biological Systems II. P B S Clarke, M. Quik and K. Thurau, (Eds.); Advances in Pharmacological Sciences, Birkhauser Publishers, pp. 293–299, 1995). Patients' tics were videotaped before treatment began and 3 hours after the start of treatment. The frequency and severity of tics were reduced 47% and 34%, respectively, at three hours. Patients with the least control by neuroleptic treatment showed more dramatic improvement than did patients whose neuroleptic treatment alone had been more effective. The effects of the TNP persisted longer than the expected 24 hours. In two patients with incapacitating TS symptoms before the TNP, the effect lasted 3 weeks to 4 months without further administration of nicotine.

To further explore the potential long-term therapeutic response to TNP in TS patients, twenty TS patients (17 children and adolescents and 3 adults), in 18 of whose tic symptoms were not controlled with neuroleptics and 2 of whom were free of medication, were followed for various lengths of time following the application of two TNPs (Silver A A et al. J Amer Acad Child & Adolescent Psychiatry, 35(12): 1631–1636, 1996; Shytle R D et al. Drug Development Research, 38(¾): 290–298, 1996). While there was a broad range of individual responses, it was determined that each application of a single TNP produced a significant reduction in Yale Global Tic Severity Scale mean scores lasting approximately 1–2 weeks. Thus, transdermal nicotine was an effective adjunct to neuroleptic therapy of TS, and helped when administered alone to two patients.

It has been observed that 50% of children presenting with TS also have Attention Deficit Hyperactivity Disorder (ADHD). ADHD is a neurobiological disorder characterized by impaired attentiveness, increased impulsivity, and hyperactivity. ADHD is now the most commonly diagnosed childhood psychiatric condition, with some 3.5 million afflicted. In addition, 60% of adolescents with ADHD continue to have symptoms in adulthood, representing another 2.5 million patients.

The current patent application is concerned with the administration of nicotine antagonists, particularly mecamylamine (3-methylamino-2,2,3-trimethylnorcamphane). Mecamylamine is well known as a nicotine antagonist and blocks ganglia which nicotine stimulates. First introduced as an anti-hypertensive, mecamylamine blocks sympathetic ganglia transmission and thereby causes vasodilatation and a fall in blood pressure (Taylor P, In: Goodman L S, Gilman A (eds) The Pharmacological Basis of Therapeutics, McMillan Publishing Co., New York City, pp. 193–95, 1996). Generalized ganglionic blockade may result also in atony of the bladder and gastrointestinal tract, impaired sexual function, cycloplegia, xerostomia, diminished perspiration and postural hypotension. While the clinical use of mecamylamine as a ganglionic agent has largely been replaced by more effective antihypertensive medications, scientists remain interested in mecamylamine because of its ability to block nicotine binding sites in the brain (see, e.g., Martin B R, Onaivi E S, Martin T J, Biochemical Pharmacology 38: 3391–3397, 1989; and Banerjee S et al, Biochemical Pharmacology 40(9): 2105–2110, 1990). These nicotine binding sites, known as nicotinic acetylcholinergic receptors (nAChr), are normally activated in the brain by acetylcholine, a prominent neurotransmitter.

Nicotine, via tobacco in various forms, has been one of the most widely utilized drugs for centuries (Wilbert J, J Ethnopharmacol 32(1–3): 179–186, 1991). Nicotine is a potent modulator of nAChrs (Changeux J P, Sci Amer (November) pp. 58–62, 1993). Through these receptors, nicotine activates the presynaptic release of several neurotransmitters including acetylcholine, norepinephrine, serotonin and dopamine (Balfour D J K, Pharmacological Therapeutics 16: 269–282 1982). Agents which can modulate central monoaminergic neurotransmissions by acting on nAChrs may be useful therapeutically for treating neuropsychiatric disorders (Jarvick M E, Br J Addict 86: 571–575, 1991; Newhouse P A, Hughes J R, Br J Addict 86: 521–526, 1991; and Hughes J, Clarke P B S (Eds): The effects of nicotine on biological systems II. Abstract S40, 1994; Decker M W et al, Life Sci 56: 545–570, 1995).

Unlike some ganglionic blocking agents, which do not readily reach the central nervous system (CNS), mecamylamine has been reported to produce central effects in humans, such as blocking the CNS actions of nicotine (Martin B R, Onaivi E S, Martin T J, Biochemical Pharmacology 38:3391–3397, 1989) and in altering cognitive functioning (Newhouse P A et al, Neuropsychopharmacology 10: 93–107, 1994), electrical brain waves (Pickworth W B, Herning R I, Henningfield J E, Pharmacology Biochemistry & Behavior 30: 149–153, 1988) and cortical blood flow (Gitalman D R, Prohovnik I, Neurobiology of Aging 13: 313–318, 1992).

While most animal studies used more than 0.5 mg/kg, Driscoll found that a small dose of only mecamylamine (<0.3 mg/kg, not 0.5 mg/kg) to high-avoidance rats increased their avoidance success almost as much as 0.1 mg/kg nicotine (but less than 0.2 mg/kg nicotine). Based on his experiments, Driscoll concluded that "mecamylamine may exert unpredictable effects on rats at the dosage levels used to block nicotine in behavioral tests" (Driscoll P., Psychopharmacologia (Berl.) 46:119–21, 1976).

In a recent study of the nicotine receptor (nicotine binding site) and its ion channel (mecamylamine binding site), Banerjee et al. disclosed that mecamylamine and several nicotine analogs have a high affinity for the mecamylamine site. Like mecamylamine, several nicotine analogs also have anti-nicotinic effects (Banerjee S et al. Biochem Pharmacol 40(9): 2105–10, 1990). Research is also proceeding on alkaloids which act on the nicotinic receptor channels (Daly J W: Alkaloids as Agonists, Antagonists and Noncompetitive Blockers of Nicotinic Receptor Channels. In: Proceedings of Nicotinic Acetylcholine Receptors as Pharmaceutical Targets. Jul. 24–25, 1997, Washington, D.C.).

Many neuropsychiatric disorders involve abnormal or involuntary movements including but not limited to obsessive-compulsive disorder (OCD), TS, ADHD, hemidystonia, and Huntington's disease. These diseases may be caused by neurochemical imbalances in the brain's basal ganglia. Acetylcholine, by activating nAChrs in the basal ganglia, regulates motor activity in humans. The action of nAChrs in the basal ganglia has been well documented (Clarke P B S, Pert A, Brain Res 348: 355–358, 1985). Nicotinic stimulation excites activity in the dopamine (DA)-producing cells in the basal ganglia (Clarke P B S et al, J Pharmacol Exper Therapeutics 246: 701–708, 1988; Grenhoff J, Aston-Jones G, Svennson T H, Acta Physiol Scand 128: 351–358, 1986; Imperato A, Mulas A, Di Chiara G, Eur J Pharmacol 132: 337–338, 1986), while mecamylamine blocks nAChr and inhibits DA release from basal ganglia structures (Ahtee L, Kaakkola S, Br J Pharmacol 62: 213–218, 1978).

U.S. Pat. No. 5,774,052 to Rose and Levin discloses agonist-antagonist combinations to reduce the use of nicotine and other drugs. In combination with nicotine, the nicotinic antagonist mecamylamine was given to treat tobacco dependency. Rose and Levin proposed including both nicotine and mecamylamine in a patch. Rose and Levin also suggested that such agonist-antagonist combinations could be used in other psychopathological disorders and cases involving neuronal dysfunction (e.g., manic depression, schizophrenia and hypertension due to sympathetic autonomic disorder).

It would benefit patients to be able to have better symptom control and fewer side effects. In particular, it would be preferable to take a single drug, as did patients in at least some of the reports disclosed herein. Our clinical experience with mecamylamine in human patients with a variety of diagnoses supports a variety of uses. Herein is disclosed improved symptom control with a nicotine antagonist (mecamylamine) alone or in combination with neuroleptics for the treatment of a variety of nicotine-responsive neuropsychiatric disorders.

BRIEF SUMMARY OF THE INVENTION

It is an object of the present invention to provide new therapy for patients with nicotine-responsive neuropsychiatric disorders.

It is a further object of the present invention to provide therapy with fewer side effects to improve patient medication compliance, as well as to improve their quality of life and social functioning.

Herein is disclosed a method of treating an individual with nicotine-responsive neuropsychiatric disorders comprising administering to the individual an effective amount of a nicotine antagonist. Preferably, the nicotine antagonist is mecamylamine, a stereoisomer, or a mecamylamine analog. The effective amount of mecamylamine is that which improves the individual's signs and symptoms. In tic disorders, the effective amount is the amount which decreases the frequency and/or severity of tics in the individual. Additionally, there may be an additional step of administering to the individual an effective amount of a neuroleptic drug. Examples of neuroleptic drugs are haloperidol, pimozide, fluphenazine, and risperidone.

Examples of nicotine-responsive disorders are movement disorders such as Tourette's Syndrome, essential tremors, hemidystonia, tardive dyskinesia, and Huntington's Disease (HD). Examples of other nicotine-responsive psychiatric disorders are schizophrenia, depression, attention deficit hyperactivity disorder, bipolar disorder, rage outbursts, and obsessive-compulsive disorder.

BRIEF DESCRIPTION OF DRAWINGS

FIG. 1 shows the chemical structures of mecamylamine and several other nicotinic antagonists.

DETAILED DESCRIPTION OF THE INVENTION

We have previously demonstrated that nicotine, when added to or substituted for haloperidol neuroleptic treatment, produced rapid and marked relief from tics and other symptoms of TS not controlled by neuroleptics alone. Using neuroleptic-induced catalepsy as a model for understanding the therapeutic actions of neuroleptics and nicotine in TS patients, it was initially proposed that nicotine potentiates the actions of D2 antagonists on catalepsy by activating disinhibited striatal cholinergic interneurons which innervate striatopallidal GABA projection neurons. Thus, an additive inhibition of the globus pallidus (Emerich D F et al, Pharmacol Biochem Behav 38:875–880, 1991) is produced. However, because nicotine has complex neuropharmacologic actions, the exact mechanism by which nicotine interacts with neuroleptics to reduce symptoms of TS has been difficult to elucidate. One hypothesis is that transdermal nicotine exerts its therapeutic effect by causing persistent inactivation of the nicotine receptor (Shytle R D et al, Drug Development Research 38(¾):290–298, 1996). A neuropharmacological action consistent with this hypothesis has been observed in vitro (Lukas R J, Drug Dev Res 38:136–48, 1996).

In a few TS patients who were not responding to the usual treatments, we found that mecamylamine, the nicotine receptor antagonist approved for the treatment of hypertension, also reduced the symptoms of TS. The improvement in TS symptoms following mecamylamine treatment alone or in combination with neuroleptics was unexpected, since one would generally expect the effects of mecamylamine to oppose those of nicotine: If fewer tics occur with nicotine, one would expect more tics with mecamylamine. Thus, the significant improvement seen in patients with mecamylamine treatment is a surprising development. We believe that in addition to mecamylamine, other nicotine receptor antagonists, discussed in detail below, also could be used. Furthermore, based on effects on co-existing illnesses, we believe that nicotine receptor antagonists are useful not only in TS, but also in such other neuropsychiatric disorders such as attention deficit hyperactivity disorder (ADHD), Obsessive Compulsive Disorder (OCD), Essential Tremor (ET), Tardive Dyskinesia (TD), Depression (D), and Huntington's Disease (HD). Nicotine antagonists can also be expected to affect other nicotine-responsive disorders (e.g., schizophrenia, depression, bipolar disorder, rage outbursts and panic states).

Hemidystonia also is nicotine responsive and is a focal movement disorder involving an arm and a leg on one side of the body. It generally develops in adulthood, remains stable and rarely spreads to other body parts. It is part of a family of syndromes which also include spasmodic torticollis (intermittent spasms turning or bowing the head). In generalized and segmental dystonias, involving more of the body, anticholinergic drugs, benzodiazepines, baclofen, carbamazepine, reserpine and levodopa have been tried for relief of symptoms. In severe focal dystonias, a dilute solution of botulinum toxin may be injected into the affected muscle, or nerves may be denervated surgically. Hemidystonia can also be expected to respond to mecamylamine.

Definitions:

"Nicotine Antagonists", of which mecamylamine is but one example are a large and growing category. A truly exhaustive list of such compounds would take up too much space here. The following discussion is not intended to be exhaustive but to teach how to identify compounds which are encompassed by this term. Currently interesting nicotinic antagonists and related compounds in research were discussed by Daly J W (ibid) which is incorporated by reference. Clark and Reuben (Br. J. Pharmacol. 117: 595–606, 1996) disclose dihydro-beta-erythroidine, methyllycaconitine, chlorisondamine, and trimethaphan. Normecamylamine, N-(1,2,2)trimethyl-1-bicyclo[2,2,1,]-heptylbenzenamine, dimethylaminoisocamphane, exoaminonorbornane, 2,2,6,6-tetramethylpiperdine, 2,2,6,6-tetramethyl4-aminopiperdine, and pempidine were identified as active nicotinic antagonists (Banerjee et al., Biochemical Pharmacology 40: 2105–2110, 1990). This article and its test methods are hereby incorporated by reference. Additional examples of nicotine antagonists include erysodine (Decker, European Journal of Pharmacology 280:79–89, 1995), phenyltropane carboxylic acid methyl esters (Lerner-Marmarosh et al., Life Sciences 56(3): PL 67–70, 1995), arylpempidine analogues (Wang et al., Life Sciences 60(15):1271–1277, 1997); ibogaine (Daly, Biochemical Pharmacology 40(9):2105–10, 1990).

In addition, the various stereoisomers and substituted analogs of mecamylamine have been tested for activity (Stone et al., J Med Pharm Chem 5(4);665–90, 1962, hereby incorporated by reference). Activity, as tested in rats by nicotine convulsions and pupil dilatation, was routinely lost with larger substitutions for the methyl groups. Both methyl or dimethyl groups on the amino group were more active than other substituents. The d form was active; however, the dl racemate appeared to be slightly more active. Consequently, we are postulating that the l form has significant activity in this use of mecamylamine. Stone et al. reported that the exo form (methylamino group lies on the same plane as the methylene bridge) was always stronger than the endo form (methylamino group lies below the methylene bridge and tends to lie within the cage created by the bridge). In addition, a partial structure, 2,2,-dimethyl-3-methylaminobutane, also was active. Slight differences in activity between different models for the d form and other analogs indicates that there may be differential activity and effectiveness in neuropsychiatric disorders.

Other compounds which may reasonably be expected to be active in this use are disclosed in U.S. Pat. No. 4,837,218 (Alkylated Bicycloalkaneamines for Neurotoxic Injury), U.S. Pat. No. 2,894,987 (N-allyl-2-aminoisocamphane), U.S. Pat. No. 3,148,118 (Analeptically Active Agents), U.S. Pat. No. 3,164,601 (Analeptically Active N-Substituted Aminonorcamphane Derivatives). These patents are incorporated by reference.

"Beneficial effect" is an observable improvement over the baseline clinically observable signs and symptoms. For example, a beneficial effect in motor disorders includes decreases in tic frequency or severity, but improvements also can be manifested indirectly through reductions in anxiety, aggressive outbursts, and premonitory urges which often precede or compound the severity of abnormal movements. Treatment effects can be quantified by clinical observations and video tape scoring. Beneficial effects in obsessive compulsive disorders include diminution in the obsessive or compulsive behavior, which can be confirmed by patient's reports. Suemaru et al (ibid) has proposed that the nicotine-induced rat tail tremor can be used to screen for compounds to treat tremors. Repeated nicotine administration can induce locomotor hyperactivity and a tail tremor in rats which is blocked with mecamylamine (0.1–1 mg/day, ip) but not by hexamethonium which does not readily enter the brain. Centrally active clonidine (-adrenergic agonist) and prazosin (-adrenergic antagonist) reduced tail tremor more markedly than hyperactivity. However, centrally active haloperidol and chlorpromazie (dopaminergic antagonists) reduced hyperactivity more markedly than tail tremor (Suemaru K., Oishi R, Gomita Y, Arch Pharm 350:153–57, 1994).

The Yale Global Tic Severity Scale (YGTTS) is the most widely used clinical assessment rating scale used to assess tic symptoms. It provides an objective measure of tic frequency of severity based on clinical observations. This scale includes a tic symptom inventory which is filled out based on the patient's personal recall of tics occurring over the previous week. Using this inventory as a guide, the clinician then rates the severity of both motor and vocal tics on five separate dimensions: number, frequency, intensity, complexity, and interference. In addition, there is also a separate rating of global impairment which characterizes the impact of the disorder on the patient's social function, self esteem, etc., over the previous week.

An objective method for rating tic symptoms employs video recording of patients. A videotape of at least five minutes is viewed and the frequency and severity of both motor and vocal tics are recorded. Video taping has proven a valuable adjunct to clinical rating systems for drug trials (Leckman J F, et al., Arch Gen Psychiatry, 48: 324–328, 1991; Shapiro E S, et al., Arch Gen Psychiatry, 46: 722–730, 1989; McConville B J, Fogelson M H, Norman A B, Klykylo W M, Manderscheid M A, Parker K W, Sanberg P R, Am J Psychiatry, 148: 793–794, 1991; Silver A A, Shytle R D, Philipp M K, Sanberg P R, The Effects of Nicotine on Biological Systems II. P B S Clarke, M. Quik and K. Thurau, (Eds.); Advances in Pharmacological Sciences, Birkhauser Publishers, pp. 293–299, 1995; Reveley M A, et al., Journal of Psychopharmacology Supplement, A30, 117, 1994) and challenge studies (Chappell P B, et al., Adv Neurol 58: 253–262, 1992; Lombroso P J et al. Neurology 41: 1984–1987, 1991). In a recent report, Chappell and colleagues (Chappell P B, et al. J Am Acad Child Adolesc Psychiatry, 33: 386–393, 1994) validated both motor and vocal tic frequency by video tape and found that such data correlated well with established clinical rating scales.

"Neuroleptic drug" as used herein is a drug which affects thinking, feeling and neurological status, particularly movement and posture (as in TS). Almost all neuroleptic drugs have a strong extrapyramidal effect, resulting in *Tardive dyskinesia* (see above). Examples of neuroleptic drugs are haloperidol (Haldol®, McNeil Pharmaceutical, Raritan, N.J.), pimozide (Orap®, Teva Pharmaceuticals, Kulpsville, Pa.), fluphenazine, and risperidone (Risperdal®, Janssen Pharmaceutical, Titusville, N.J.).

The term "effective amount" refers to the amount of nicotine antagonist that is necessary to provide benefit. The precise amount required will vary depending upon the particular compound selected, the age and weight of the subject, severity of the disorder, route of administration, and so forth, but may easily be determined by routine experimentation, as described below in the clinical examples. In general, however, an effective amount will range from about 0.001 mg/kg to about 6 mg/kg per day, preferably about 0.002 mg/kg to about 3 mg/kg, more preferably about 0.005 mg/kg to about 2 mg/kg, and most preferably about 0.01 to about 1.5 mg/kg. A starting dose for adults with drug-resistant TS is about 2.5 mg per day, with dosage adjusted according to return of symptoms (see case histories below). A small child with mild ADHD preferably starts with 1 mg per day or less. The effective amount of a neuroleptic drug is the least amount which when combined with a nicotine antagonist relieves symptoms. Our clinical experience suggests some patients may not require any neuroleptic drug to achieve maximum benefit.

The term "pharmaceutically acceptable" refers to a lack of unacceptable toxicity in a compound, such as a salt or excipient. Pharmaceutically acceptable salts include inorganic anions such as chloride, bromide, iodide, sulfate, sulfite, nitrate, nitrite, phosphate, and the like, and organic anions such as acetate, malonate, pyruvate, propionate, cinnamate, tosylate, citrate, and the like. Pharmaceutically acceptable excipients are described at length by E. W. Martin, in Remington's Pharmaceutical Sciences (Mack Pub. Co.).

Pharmaceutical compositions containing nicotine antagonists may contain one or more pharmaceutical carriers. The term "pharmaceutically acceptable carrier" refers to any generally acceptable excipient that is relatively inert, non-toxic and non-irritating. When the carrier serves as a diluent, it may be solid, semisolid, or liquid material acting as a vehicle, excipient, or medium for the active ingredient. Pharmaceutical unit dosage forms may be prepared for administration by any of several routes, including, but not limited to, oral and parenteral (especially by intramuscular and intravenous injection, or by subcutaneous implant or transdermal administration). Representative of such forms are tablets, soft and hard gelatin capsules, powders, lozenges, chewing gums, emulsions, suspensions, syrups, solutions, sterile injectable solutions, and sterile packaged powders. Compositions containing nicotine antagonists may be formulated by procedures known in the art so as to provide rapid, sustained, or delayed release of any or all of the compounds after administration.

As the nicotine antagonist formulation of the present invention is well suited to oral administration, preferred carriers facilitate formulation in tablet or capsule form. Solid pharmaceutical excipients such as magnesium stearate, calcium carbonate, silica, starch, sucrose, dextrose, polyethylene glycol (PEG), talc, and the like may be used with other conventional pharmaceutical adjuvants including fillers, lubricants, wetting agents, preserving agents, disintegrating agents, flavoring agents, and binders such as gelatin, gum arabic, cellulose, methylcellulose, and the like, to form admixtures which may be used as such or may be tabulated, encapsulated, or prepared in other suitable forms as noted above. A general description of formulation is given in Remington's Pharmaceutical Sciences (Mack Pub. Co.).

Administration

Administration is preferably by oral dosage but may be by transdermal application, intranasal spray, bronchial inhalation, suppository, parenteral injection (e.g., intramuscular or intravenous injection), and the like. Carriers for parenteral administration include, without limitation, aqueous solutions of dextrose, mannitol, mannose, sorbitol, saline, pure water, ethanol, glycerol, propylene glycol, peanut oil, sesame oil, polyoxyethylene-polyoxypropylene block polymers, and the like. One may additionally include suitable preservatives, stabilizers, antioxidants, antimicrobials and buffering agents, for example, BHA, BHT, citric acid, ascorbic acid, tetracycline, and the like. Alternatively, one may incorporate or encapsulate the nicotine antagonist formulation in a suitable polymer matrix or membrane, thus providing a sustained-release delivery device suitable for implantation or application to the skin. Other devices include indwelling catheters and devices such as the Alzet® minipump.

The invention has been disclosed by direct description. The following are examples showing the efficacy of the method in providing benefit. The examples are only examples and should not be taken in any way as limiting to the scope of the method.

EXAMPLES

Clinical Examples

Patient 1 was a tall, 173-pound, 15-year-old male diagnosed with TS. He had been a patient in our clinic, receiving 2 mg of haloperidol daily and two transdermal nicotine patches (14 mg/24 hr) each week for approximately one year for effective control of severe symptoms of TS. However, approximately two months before a scheduled follow-up visit, his tics, which had been under excellent control, had emerged again. At that time, his haloperidol dose was increased to 3 mg/day and the frequency of nicotine patch application was increased to every other day, with some improvement noted. However, the side effects of the nicotine patch, particularly nausea, were disturbing to the patient, resulting in his refusal to wear the patch. In addition, because of the increased risk of nicotine addiction with daily use, we were reluctant to subject the patient to continued use of the patch.

Two weeks before his visit to our clinic, the nicotine patch was discontinued. Eye-blinking, eyebrow raising, facial grimacing, head jerks, abdominal tics, and leg/foot movements were present. His score on the YGTSS was 17/30; his tics totaled 245 over a 5-minute period with overall severity rated as 3 (moderate) on a 7-point scale.

Mecamylamine (5 mg) was given orally at about 11:30 AM. Approximately two hours later, the patient reported that his urge to tic was reduced. The YGTSS score was 6/20. Although tics were still present, there was a 25% decrease in tic frequency. Overall tic severity was reduced by 50%. By 6:00 PM, his mother reported that the patient felt better, there were virtually no tics present, and there were no side effects. However, by the next morning, his tics were beginning to return. One month later, on a daily dose of 5 mg mecamylamine at breakfast, his tics were still under control, and the patient reported that he was more relaxed and alert. The shy, taciturn youth of 30 days earlier was now more outgoing and voluble.

The clinical experience of treating this first patient suggested that, in combination with haloperidol, mecamylamine could be used to suppress motor tics. The effect of mecamylamine after a single oral dose was seen in 2–3 hours and lasted approximately 8–12 hours. The daily dose of mecamylamine has been continued for 211 days without adverse effects.

Patient 2 was a 16-year-old in the ninth grade whose overall cognitive functioning was in the high-average range but he had a severe deficit in visual-motor function. He developed motor and vocal tics at 10 years of age, within six months after starting on methylphenidate and Dexedrine (dextroamphetamine sulfate, SmithKline Beecham Pharmaceuticals, Philadelphia, Pa.) for attention deficit disorder and academic difficulty. With 0.1 mg of clonidine three times a day, his tics were said by his parents to be under control. However, for the past two years, he has taken no medication for motor and vocal tics. By the end of eighth grade, he had failed math, received C and D grades in his other subjects and had marked difficulty with any visual-motor function. His handwriting was slow and labored; he resisted any written work, became frustrated with it, and felt that he was doomed to failure. On his visit to our clinic, his tics were clearly evident: eye blinking, mouth grimacing, gross body tics, quick and jerky movements of his shoulders, head tics, and sniffing. He complained that he was "active in his head" (distractible). During the summer he was attempting to learn math so that he could retake the examination and enter high school in the fall. However, he was having difficulty writing down the steps needed to answer the math problems (as is required in the examination) although he can "get the steps in his head." He was impatient, frustrated and giving up.

Mecamylamine was prescribed and the patient was told to take it after dinner. His mother, a nurse, reported that two hours after taking 5 mg of mecamylamine he started to study math. This time, he was patient, felt his "mind is clearer", was more relaxed, and worked on math problems for three hours without distraction. His tics had subsided in intensity and frequency. The following morning, he felt restless; and tics started to return, though not as disturbing as previously. He had eye blinking and gross, jerky body movements. He was prescribed 5 mg mecamylamine at breakfast and 2.5 mg after dinner daily. Twelve days later, the patient reported that with the medication, he was not "hyper" and could concentrate on his schoolwork. The tics, although occasionally present, had subsided. His blood pressure was unchanged at 114/80. In this patient, no neuroleptic drugs were given in combination with mecamylamine, which suggests that mecamylamine alone can suppress TS symptoms. After eight weeks of treatment, the patient's mother reported that he was doing fine and wanted to continue therapy and had entered high school. He continued on mecamylamine for 208 days with no adverse side effects.

Patient 3 was a 35-year-old, who has had TS with severe motor and vocal tics, obsessions and compulsions since the age of six. She is the mother of three children, the oldest of whom, a girl aged 12, also had TS. Over several years, a variety of medications had been tried, including Zoloft (sertraline hydrochloride, Roerig Div, Pfizer, New York City) to limit her depression and mood swings. In June 1996, with a trial of the taansdermal nicotine patch (7 mg) given in our clinic, her tics subsided within three hours. However, in the next 24 hours, knee, ankle and wrist joints became painful and swollen; and the patch was discontinued. A trial dose of haloperidol (0.5 mg) was then given. In 12 hours, she experienced a precipitous rise in temperature which necessitated discontinuation of haloperidol. On follow-up at our clinic one year later, she was tense and unhappy and displayed multiple and severe tics, almost continual eye blinking, grimacing, nose twitching, sniffing, and a compulsive need for everything to be "just right" in her home.

She was started on 5 mg mecamylamine at 2 PM. At 5 PM there was a distinct obtundation of tics which, although still present, were markedly reduced (50%) in intensity. She was continued on 5 mg mecamylamine for 4 days and reported that the tics were still present but less intense. She reported feeling relaxed with decreased anxiety. Moreover, she reported that her urges to have rage outbursts during stressful situations were reduced while taking mecamylamine. The daily dose of mecamylamine was continued for 30 days with no appreciable change in blood pressure or heart rate. She complained of constipation during her menses, but reported no other side effects. When her prescription for mecamylamine ran out, she requested that the mecamylamine be continued. In this patient, as with patient 2, a neuroleptic was not necessary. She had been on mecamylamine for 195 days, and then in a check-up call, she said she had discontinued taking the mecamylamine because although she appreciated her moods being less volatile, she missed her "highs."

Patient 4 was a 43-year-old salesman with a history of TS since age 14. He had received haloperidol (0.5 mg bid) and a 14 mg transdermal nicotine patch twice each week for the previous 6 months, without complete control of motor or vocal tics. Rather than increase the haloperidol dose or increase the frequency of nicotine patch, the nicotine patch was discontinued and mecamylamine (5 mg per day) was prescribed. At baseline, the YGTSS was 27/30, and a 5-minute segment of videotape revealed a total tic count of 207 with an overall severity of 4 (very noticeable) on a 7-point scale. Approximately 90 minutes after the first dose of mecamylamine, the patient reported that he felt more relaxed; his YGTSS score was 20/20; and severity was 2.5 (slightly noticeable). Six hours later, the patient reported that his feeling of relaxation persisted, and the facial grimacing and head jerks were not apparent. His eye blinking, although still occurring, was decreased in severity. However, by the next morning, the tics were beginning to return. With 5 mg mecamylamine at breakfast, obtundation of tics within 1–2 hours was again apparent. Approximately eight hours later the tics began to return. An additional dose of 2.5 mg mecamylamine before dinner was prescribed. This dose controlled motor and vocal tics during the evening. A maintenance dose of 5 mg mecamylamine with breakfast and 2.5 mg before dinner was prescribed. Haloperidol (0.5 mg bid) was continued. Nicotine was discontinued. The combined use of mecamylamine and haloperidol, each in small doses, controlled motor and vocal tics.

Recently patient 4 reported that his primary care physician could not find a cause for his chronic fatigue which had started before mecamylamine treatment. There was no change in blood pressure. However, the patient discontinued mecamylamine and resumed the nicotine patch.

Patient 5 was an 18-year-old male who was first seen in our clinic at age 15. His TS symptoms had been treated with pimozide (Orap, Teva Pharmaceuticals, Kulpsville, Pa.) up to 16 mg daily since age 10. He had a strong family history of tic spectrum disorders. His mother, maternal grandfather, maternal uncle and a male cousin all had evidence of Tourette symptoms. At his initial clinic visit, he was receiving 12 mg of pimozide together with Prozac® (fluoxetine hydrochloride, Eli Lilly & Co., Indianapolis Ind.). His motor tics were minimal but he was depressed with severe Parkinsonian-like facies and a fine motor tremor of his hands aggravated by intention. Decreasing pimozide to 4 mg daily and discontinuing Prozac resulted in relief of both depression and Parkinsonian-like symptoms, except for the persistent hand tremor. During the course of his treatment with us, an abnormal EEG with mild background disorganization and sharp activity lateralized to the left temporal region was found. He was treated with carbamazepine, haloperidol and Cogentin® (benztropine mesylate, Merck & Co., West Point, Pa.) with marked reduction in motor and vocal tics. However, the tremors persisted, and obsessive and compulsive symptoms became prominent. He said he could not focus on a task because his mind was "wandering to something else". A trial of nicotine patch resulted in nausea, headache and noncompliance. Two months later on a visit to the clinic, a trial of mecamylamine 2.5 mg was given. Within two hours, this patient said, "I feel really calm", and he said feeling like this, he could go back to his community college studies. In addition, the hand tremor, so pronounced before mecamylamine administration, had almost disappeared.

Patient 6 was a 23-year-old male, who had had severe Tourette symptoms since he was in second grade. Over the years he had been treated with a variety of neuroleptic medications as well as clonidine and clonazepam (Klonopin®, Roche Laboratories, Nutley, N.J.) At his first visit to our clinic, he had been receiving 12 mg of pimozide daily for at least two years, and was working as a counselor at a camp for emotionally disturbed children. Twice he had failed his courses to become an Emergency Medical Technician. His Tourette symptoms were among the most severe seen at our clinic. He was in constant restless motion, his speech was under pressure, there were tic-like grimaces on his face, shrugging of his shoulders, copropraxia (his fingers darting to his groin), but most prominent was coprolalia. Every other word was punctuated with an expletive, sexual in nature, under pressure, distinct, and loud. He tried to cover up using a smile and joviality. However, he was frightened and depressed and had a significant tremor of his fingers. On neuropsychological testing, severe visual-motor problems were evident. A trial of 7 mg transdermal nicotine resulted in a mild decrease in intensity of his tics and coprolalia. However, within 4 hours he became nauseous and dizzy. Nicotine patch was tried daily for one week increasing the time it was applied. However, side effects continued, and nicotine was discontinued.

After a 2-week washout of nicotine, 2.5 mg mecamylamine daily was prescribed. At the end of 7 days, the patient reported that about 70% of his coprolalia had subsided. Follow-up at that time confirmed not only the significant decrease in coprolalia, but now what remained was whispered. His restlessness too subsided as did the facial grimaces. Only a trace of hand tremor remained.

Patient 7, a 16-year-old female high school student, was first seen in our clinic in July 1997, has a long history of Tourette's Syndrome, obsessive-compulsive disorder and depression for which she has been receiving Klonopin 1 mg tid with minimal improvement in tics. With the addition of sertraline 25 mg bid and transdermal nicotine patch there was a noticeable improvement in tics and in mood. However, the side effects of the nicotine patch including headaches and nausea prompted discontinuing the nicotine patch. In mid-August 1997, mecamylamine 2.5 mg was prescribed, sertraline gradually discontinued and Klonopin reduced to 1 mg/day. Within 2 to 3 days, she reported tics "remarkably diminished", mood improved with decreased irritability. In early December 1997, however, her mother reported "aggression and self doubt" had started again, and a sniffing vocal tic returned. Increasing mecamylamine to 3.75 mg daily was accompanied by relief of depression, moodiness and irritability, moderate improvement of tics (+4 to +5 on a scale of 10) improvement in attitude to school and friends. There have been no complaints of mecamylamine side effects.

Patient 8, a small, wiry 9 year old, had been diagnosed as having ADHD at 5 years of age and had received methylphenidate (20 mg bid) for approximately 6 months before being seen in our clinic. Although methylphenidate did help with attention and decreased his compulsivity, he developed motor tics within 4 months of its use. Methylphenidate use then discontinued and he proved to be intolerant of a 7 mg transdermal nicotine patch because of nausea. Mecamylamine 2.5 mg was only minimally effective, 3.75 mg daily, however, reduced his hyperactivity and helped him sustain attention. He said he felt better and the "demon's voice" he no longer heard. On the global improvement scale, his mother rated him as a +3 on a scale of 10. There has been no reported side effects in 210 days.

Patient 9 had been seen in our clinic when he was 11 months of age. His oppositional behavior was such that his mother sent him to live with his a paternal uncle in another state. Seen in our clinic again at age 14, his motor and vocal tics were still severe; but he was now willing to consider treatment. Risperidone (2 mg/day) and transdermal nicotine patch 7 mg/day (approximately 2 patches per week) relieved his symptoms. However, he was still moody, irritable, and demanding. Mecamylamine 2.5 mg daily was added. Within 3 weeks his mother reported that since mecamylamine was added he has "the best improvement he has ever made", he is much calmer, his eye blinking tic has subsided, and outbursts of rage have decreased. During telephone follow up 6 months after mecamylamine was started, his grandmother reported that patient 9 had discontinued risperidone on his own initiative and on his own initiative too, and that he had discontinued mecamylamine after about 5 months of therapy. He continued to use a nicotine patch with a frequency of "usually more than one each week". She reported that his tics were mostly under control; however, he is demanding and has occasional rages.

Patient 10 was a 37-year-old alcoholic smoker, who was depressed, had severe and incapacitating coprolalia and anxiety attacks, had been treated with antidepressants, benzodiazepines, and with haloperidol with limited relief of symptoms. Compliance in use of medications, however, was inconsistent. Mecamylamine, 2.5 mg daily was started on Jul. 1, 1997. The patient reported that he was "more relaxed, speaks better [coprolalia diminished], and speech more fluent". However, he complained of "headaches and heartburn". Mecamylamine was tried again on Dec. 8, 1997. On initial dose of 2.5 mg, coprolalia was under control for about 1 hour, following which the patient complained of "getting jittery and nervous". Mecamylamine was discontinued.

Patient 11 was a 14-year-old boy with Tourette's Syndrome, ADHD, OCD, severe visual and motor dysfunction, anxiety, and low self esteem. An avulsion of his thumb contributed to his feeling of being "incomplete" and physically different from his class mates. His symptoms were under moderate control with haloperidol. Transdermal nicotine potentiated the therapeutic effect of haloperidol, but he never was comfortable with the patch and finally rejected nicotine because of nausea. On Jul. 17, 1997, mecamylamine at 2.5 mg per day was started. Within 3 hours of the first dose the patient was less restless and felt calm. His tics had markedly decreased in severity. There were no adverse effects and blood pressure remained at 110–114/70–76. Within the week after mecamylamine was started, his mother reported a marked improvement in mood and behavior, decreased irritability and pleasant interactions with parents. "He does not hit his little brother any more." Haloperidol and clonidine, which had been continued, were decreased in dose. Mecamylamine was continued for 215 days. During this time, he had "excellent improvemenf" in terms of mood, behavior and attitude toward school. However, he had a persistent cough which did not remit. In an attempt to relieve the cough, mecamylamine was discontinued and sertraline started. The troublesome cough then occurred only at meal times. Return to mecamylamine is under consideration.

Patient 12 was started on methylphenidate for distractibility and hyperactivity when he was 9. Tics began within months of starting methylphenidate. The symptoms of Tourette's syndrome, OCD, and ADHD had become progressively worse. He had received a combination of medication including pimozide, haloperidol, Prozac, and Paxil, together which caused mild control of his tics, increased depression and sleeping in school, so much so that he was removed from his current grade (8th) at school and was home-schooled for 2 months before he was brought to our clinic at age 14.5 years. Gradually decreasing his various medications to haloperidol 2 mg and adding clonidine did not significantly alter his symptoms. Transdermal nicotine patch (7 mg) twice weekly did obtund his symptoms. However, when nicotine was discontinued and mecamylamine 3.75 mg/day was added, there was definite improvement in motor and vocal tics. Although still present, the tics are markedly obtunded and of low intensity. His mood is relaxed. He is doing well in school and is participating in high school athletic programs. Immaturities in the Bender-Gestalt test are no longer present. His blood pressure on December, 1997 was 114/80; on Jun. 12, 1998, 100/70. There were no complaints.

Patient 13 was a 12-year-old boy had been seen in our clinic since he was 9 years of age. Motor and vocal tics, and compulsions have become increasingly worse after the age of 4 years, more so after 7 years. Repeat EEG's were abnormal "dysrhythmia grade III, bilateral synchronous and independent central, parietal temporal spikes". Tegretol aggravated all symptoms. His motor and vocal tics have been difficult to control with standard medication; he was sensitive to nicotine which, although helping obtund his tics, caused intolerable side effects. On Aug. 13, 1997, mecamylamine, 2.5 mg/day, was started. The patient reported that "I was calmed down, not grunting so hard." However, his improvement lasted only 3 to 5 days when tics started up again, and headaches became severe. Increasing the dose to 5 mg/day did not decrease tics but did increase headaches. Blood pressure which usually was between 110/76, went down to 90/68; pulse rate usually between 70 and 76, was 68. Mecamylamine was discontinued.

Patient 14 was an unusual 9-year-old boy, dysplastic in appearance, physically small, triangular shaped head, in constant movement, and chattering about his obsessions of guns and weapons. He had severe motor and vocal tics, coprolalia, compulsive touching, marked anxiety. He had received various medications including carbamazepine, methylphenidate, both of which only increased activity. Haloperidol reduced his activity but its effect lasted only about 3 weeks. A transdermal nicotine patch (7 mg) only made him nauseous. Mecamylamine on a 1.25 mg dose per day also appeared to increase his restlessness and make him weepy and irritable. It was discontinued after 10 days.

Summary of Findings: Twelve of the fourteen patients described reported improvement in tics and in mood following mecamylamine. All but one patient reported feeling more relaxed. The mood swings of the two female patients were decreased on medication. At the doses administered, there was one patient with significant blood pressure changes. Because mecamylamine at higher doses is approved for hypertension, the lower doses should be and were well tolerated. These patients had multiple problems: Besides TS, patient 2 had ADHD and obsessive thoughts which were both helped by the new therapy; and patients 3 and 7 also had compulsive behavior which decreased with mecamylamine treatment. In addition, patient 5 had a tremor of the hand which was reduced following mecamylamine administration. In this group of patients treated with mecamylamine, there was a reduction in symptoms of inattention, hyperactivity, tremor, obsessive compulsive behavior, depression and mood swings, in addition to the motor and vocal tics of Tourette's syndrome.

Dosages for these TS patients whose condition was not under control with conventional therapy are summarized below in Table 1. Dosages ranged from about 0.03 to 0.10 mg/kg. This range was used to calculate Table 2.

TABLE 1

Tested Therapeutic Doses of Mecamylamine (Inversine ®)

| Sex | Diagnosis | Age | Daily Dose (mg) | Weight (lbs) | (kg) | mg/kg |
|---|---|---|---|---|---|---|
| M | TS | 15 | 5 | 173 | 78.64 | 0.06358 |
| M | TS | 44 | 5 | 183 | 83.18 | 0.06011 |
| F | TS,OCD,D | 35 | 5 | 131 | 59.55 | 0.08397 |
| M | TS | 18 | 2.5* | 152 | 69.09 | 0.036 |
| M | ADHD,TS | 16 | 7.5 | 163 | 74.09 | 0.10123 |
| M | TS | 36 | 2.5 | 155 | 70.45 | 0.03548 |
| M | ADHD,TS | 14 | 2.5 | 170 | 77.27 | 0.03235 |
| M | TS | 23 | 2.5 | 146 | 66.36 | 0.03767 |
| F | TS,OCD,D | 16 | 2.5 | 125+ | 56.81 | 0.044 |

*While 2.5 mg/day effectively controlled hand tremors in this patient, reducing the daily dose to 1.25 mg/day resulted in a return of tremors.
+Estimated

TABLE 2

Estimated Therapeutic Dose Ranges According to Body Weight

| Body Weight (lbs) | Daily Therapeutic Dosage Range* (mg) | |
|---|---|---|
| | Low dose (mg) | High dose (mg) |
| 55 | 0.75 | 2.5 |
| 75 | 1 | 3.5 |
| 95 | 1.25 | 4.5 |
| 115 | 1.75 | 5 |
| 135 | 2 | 5.5 |
| 155 | 2.25 | 6.5 |
| 175 | 2.5 | 7.5 |
| 195 | 2.75 | 8.5 |
| 215 | 3 | 9.5 |

*Based on the tested range of 0.03–0.10 mg/kg

Other Uses

Recent reports suggest that nicotine reduces the symptoms of schizophrenia (Adler L E et al, Am J Psychiatry 150: 1856–1861, 1993), Attention Deficit Hyperactivity Disorder (ADHD) (Levin ED et al, Psychopharmacology 123: 55–62, 1995) and depression (Salín-Pascual R J et al, Psychopharmacology 121(4): 476–479, 1995). While it is generally believed that nAChr activation is responsible for nicotine's therapeutic actions in these "nicotine-responsive" disorders (Decker M W et al, Life Sci, 56: 545–570, 1995), it is clear that, like many other drugs, nicotine has complex neuropharmacological effects. Thus, many people with such nicotine-responsive disorders, could be helped with a nAChr blocker which has been disclosed herein with the example of mecamylamine, a nAChr blocker, which reduced the symptoms in the nicotine responsive disorders, TS and ADHD.

Schizophrenia, a psychiatric disorder theorized to involve hyperdopaminergic tone, is most often treated with neuroleptics, but there is now speculation that it is a nicotine-responsive disorder. For example, surveys of schizophrenic patients have demonstrated rates of smoking between 74% and 92%, compared to 35% to 54% for all psychiatric patients and 30%–35% for the general population. It has been speculated that cigarette smoking may improve underlying psychopathology by enhancing concentration and reducing anxiety from hyperarousal (Gopalaswamy A K, Morgan R, Br J Psychiatry, 149: 523, 1986). In addition, nicotine may have some role to play in reducing the cognitive deficits associated with schizophrenia and neuroleptic treatment. Cigarette smoking has been found to normalize sensory gating deficits in schizophrenic patients (Adler L E et al, Am J Psychiatry 150:1856–1861, 1993) and a recent study found that transdermal nicotine reversed some of the adverse cognitive effects of standard anti-psychotic medication and improved cognitive performance in general for schizophrenic patients (Levin E D et al, Psychopharmacology 123:55–63, 1996). If as we now hypothesize that nicotine administration may actually have a similar effect as a nAChr blocker, then it is possible that a nAChr blocker such as mecamylamine and related compounds would also reverse the adverse cognitive effects of the anti-psychotic medication and improve cognitive performance in schizophrenic patients. Moreover, since nicotine potentiates the therapeutic effects of neuroleptics in TS (McConville B J et al, Biological Psychiatry 31:832–840, 1992), the use of mecamylamine as an adjunct to neuroleptics in "neuroleptic-responsive" disorders such as schizophrenia and Huntington's chorea, can allow for reducing the neuroleptic dose, thereby reducing the side effects of the neuroleptic without reducing its therapeutic effects.

The foregoing description and examples are intended only to illustrate, not lirnit, the disclosed invention.

We claim:

1. A method of treating nicotine-responsive psychiatric disorders in individuals in need thereof, said method comprising administering to the individual an effective amount of a nicotine anttagonist.

2. The method of claim 1, wherein the nicotine antagonist is mecamylamine, a mecamylamine stereoisomer or a mecamylamine analog.

3. The method of claim 1, wherein the nicotine-responsive psychiatric disorder is schizophrenia, depression, bipolar disease, rage outbursts, attention deficit hyperactivity disorder, or obsessive-compulsive disorder.

4. A method of treating Tourette's Syndrome in an individual in need thereof, said method comprising administering to the individual an effective amount of a nicotine antagonist.

5. The method of claim 4, wherein the effective amount is the amount which decreases the frequency or severity of tics in the individual.

6. The method of claim 4, wherein the nicotine antagonist is mecamylamine, a mecamylamine stereoisomer or a mecamylamine analog.

7. The method of claim 4, wherein the nicotine antagonist is mecamylamine.

8. A method of treating attention deficit hyperactivity disorder in an individual in need thereof, said method comprising administenng to the individual an effective amount of a nicotine antagonist.

9. A method of treating a nicotine-responsive movement disorder in an individual in need thereof, said method comprising administering to the individual an effective amount of a nicotine antagonist.

10. The method of claim 9 comprising an additional step of administering to the individual an effective amount of a neuroleptic drug.

11. The method of claim 9, wherein the nicotine-responsive movement disorder is selected from the group consisting of Tourette's Syndrome, hemidystonic and tardive dyskinesia.

* * * * *